United States Patent [19]

Worley

[11] 4,192,188

[45] Mar. 11, 1980

[54] CATALYST SAMPLER DEVICE

[75] Inventor: Arthur C. Worley, Mt. Tabor, N.J.

[73] Assignee: Exxon Research & Engineering Co., Florham Park, N.J.

[21] Appl. No.: 901,440

[22] Filed: May 1, 1978

[51] Int. Cl.² .............................................. G01N 1/10
[52] U.S. Cl. ..................................................... 73/424
[58] Field of Search ................. 73/424, 421 B, 423 R; 222/370, 453

[56] References Cited

U.S. PATENT DOCUMENTS

| | | | |
|---|---|---|---|
| 1,966,712 | 7/1934 | Fisher et al. | 73/423 X |
| 2,516,097 | 7/1950 | Woodham et al. | 73/421 B |
| 2,896,444 | 7/1959 | Forman et al. | 73/423 R |
| 2,973,645 | 3/1961 | Grimes et al. | 73/424 |
| 3,129,590 | 4/1964 | Ellis | 73/324 |
| 3,319,469 | 5/1967 | Hartung | 73/421 B |
| 3,348,419 | 10/1967 | Addison | 73/424 |
| 4,009,618 | 3/1977 | Chatham | 73/424 |

Primary Examiner—Daniel M. Yasich
Attorney, Agent, or Firm—James H. Callwood; Edward H. Mazer

[57] ABSTRACT

A bottom vessel head mounted tube within a tube assembly is used to retrieve particulate matter from a fixed bed reactor. Particulate matter enters the device through coinciding inlet ports in the tubes and flows by gravity to the bottom of the inner tube. By shifting the alignment of the inlet ports, flow is stopped and the catalyst sample flows by gravity into a valved receiver which is depressurized before catalyst is recovered. The device samples catalyst at one elevation.

5 Claims, 3 Drawing Figures

CATALYST SAMPLER DEVICE

BACKGROUND OF THE INVENTION

1. Field of the Invention

The present invention relates to an apparatus for the retrieval of particulate matter from a fixed bed reactor. More particularly, the invention relates to a device for safely withdrawing samples of particulate material such as catalyst from a reaction vessel while it is operating at sub or super atmoshperic conditions without altering such conditions.

2. Description of the Prior Art

A number of prior art apparatuses have been devised for the retrieval of samples of particulate matter from fixed bed reactors. U.S. Pat. No. 2,973,645, to W. W. Grimes et al discloses a device which functions by rotation of an inner catalyst sample enclosure within an external guide tube. The device shown appears to be designed for sampling of catalyst near the bottom of the reactor. A tubular screen is extended upward into the catalyst bed from the top of the sample device. Since the cylindrical screen will be filled with catalyst when the vessel is filled, samples taken of catalyst will be from the level at the entrance to the sample closure. If the volume of the sample is small compared to the volume within the cylindrical screen, a representative sample from the level where the cylindrical screen ends could not be possible.

This type screen construction most likely would suffer severe distortion since the rather flexible screen would tend to thermally expand upward but be restrained by the catalyst, and accordingly, would be deformed and possibly rendered inoperative. Rotating the inner component of the sampler also requires that the shaft be sized for torsion. If high friction forces are involved torsional distortion is likely due to the shaft being weakened by the catalyst ports provided.

U.S. Pat. No. 3,129,590 to J. R. B. Ellis also discloses a device which terminates within the cayalyst bed with the catalyst sample being retrieved by rotation of an inner member. The device would be susceptible to deformation and/or malfunction since the sampler is terminated in the bed which will restrain the device from thermal movement when it expands. The probe is also angled inward which tends to further increase deformation due to a horizontal component of thermal expansion. Any deformation would lead to increased torsional friction due to interaction between the outer tube and inner member.

U.S. Pat. No. 3,348,419 to G. E. Addison also uses rotation between an inner and outer tube for retrieving of a catalyst sample through an elongated slot (port). The device terminates in the bed which makes the probe susceptible to deformation from restraint of the bed similar to that of J. R. B. Ellis.

U.S. Pat. No. 3,561,274 to W. M. Haunschild discloses a device which operates by using a rotating disc on top where a hole in the disc permits catalyst to flow into the probe when its port is in alignment with the hole in the top disc. This device must terminate in the catalyst bed and for this reason it is susceptible to deformation and malfunction similar to the patents by Addison, Ellis, and Hensel. Furthermore, the disc must be turned while it is buried in catalyst. This increases the friction considerably and makes the mechanism vulnerable to torsional shaft failure.

U.S. Pat. No. 3,442,138 to W. C. Hensel discloses a device which utilizes a catalyst sample capsule to limit the amount of sample to be taken. It operates by axial displacement and two versions of internal sample capsule are shown. The device terminates in the bed which makes it susceptible to deformation and malfunction similar to the devices by G. E. Addison and J. R. B. Ellis.

U.S. Pat. No. 3,319,469 to R. L. Hartung discloses a device which samples catalyst from a number of catalyst beds in one vessel. This is achieved by axial movement of an inner tube within an outer tube, each provided with coinciding port openings. Because of the extension traverse that the device must handle, it is possible that the vessel would have to be elevated above that normally used to make room for the sampling device retrieving section. The positioning of the inner probe also requires that the inlet port for sample taking and outlet port for retrieving the sample at each bed level must be accurately aligned since nonalignment of the ports, e.g. $\frac{3}{8}$" diameter holes will cause malfunction of the probe. All of this must be done from an external position below the vessel. When taking into consideration thermal expansion, i.e. the upward movement of the probe assembly the uppermost point would expand approximately 4 inches upward. If the inner tube did not move this amount, it would be impossible to insure from an external position that the port in the inner tube was in alignment with the port in the external tube of the probe. The device, therefore, would be extremely complex and impractical or difficult to use with assurance of satisfactory function. The device extends past the upper level of the bed and this will reduce the tendency for buckling since the catalyst bed only restrains thermal movement of the probe by axial friction of catalyst against the outer surface of the probe.

All of the devices described in prior art patents exhibit undesirable characteristics which limit their effective utilization for the retrieval of particulate samples from fixed bed reactors without interrupting the reaction process. Now, in accordance with the present invention, an apparatus has been devised where consideration has been given to avoiding thermal and bed weight distortion by limiting sampling to one bed level, thereby limiting overall length, and by letting the probe extend vertically through the bed, terminating in an empty space above the bed, even though the inlet port, i.e. sampling location may be located at any point in the bed. The device functions by axial displacement of an inner tube with respect to an outer tube. Since only one sample location is considered, the device is less likely to malfunction. The extension above the bed level permits venting of the probe and avoids the deformation associated with the restraint of the bed weight of prior art devices. The device is adaptable for installation in existing units without requiring special vessel shell nozzles and can be assembled in prefabricated sections. Thus, the device exhibits the beneficial characteristics of avoiding thermal distortion, bed weight distortion, simplicity, and ease of installation in existing units.

DETAILED DESCRIPTION OF THE INVENTION

Figure 1:
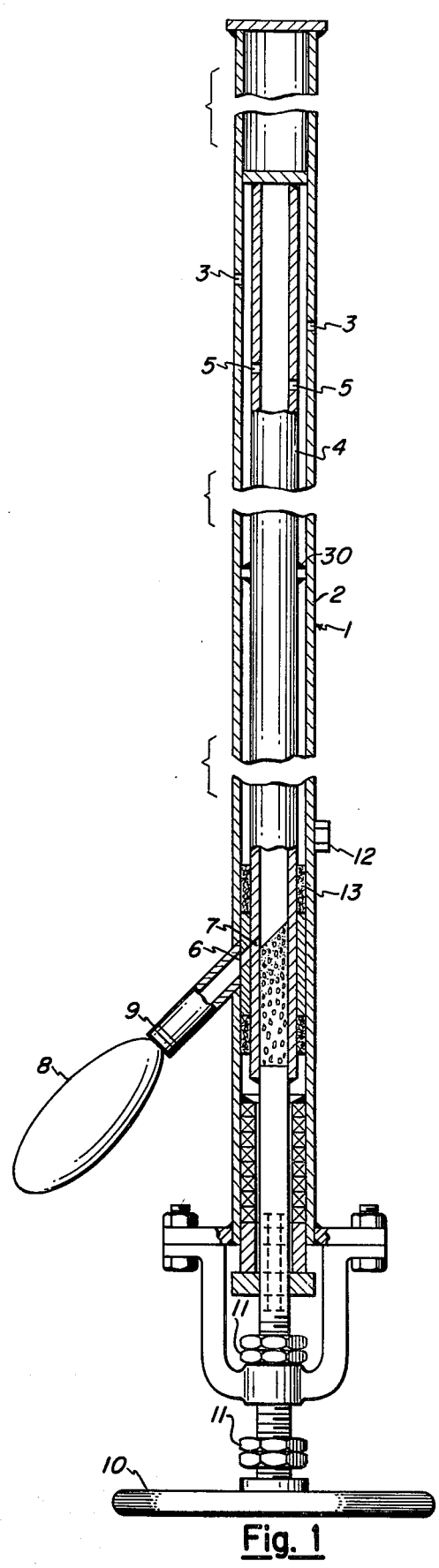
FIG. 1 is a cross-sectional vertical representation of the apparatus of the present invention.

Referring now to the drawings and in particular in FIG. 1, the sampler, generally indicated as 1 is shown in cross-sectional view. It is comprised of outer tube 2 which has outer tube inlet means such as inlet ports 3, the tube secured to the vessel to form a pressure tight connection therewith. Within outer tube 2 is inner tube 4 which has inner tube inlet means such as inlet ports 5. At the lower end of outer tube 2 and inner tube 4 are outer tube outlet means such as outlet port 6 and inner tube outlet port 7. Outer tube outlet means such as outlet ports 6 and inner tube outlet ports 7 allow for the exit of particulate matter into a means for collecting particulate matter connected in pressure sealed engagement with the outer tube outlet means, such as catalyst receiver 8. Catalyst receiver 8 contains block valve 9. At the lower end of the sampler is a means such as a shaft of a handwheel 10 which is utilized to move inner tube 4 vertically to bring inner tube inlet ports 5 and outer tube inlet ports 3 into communication so that catalyst can enter and flow to the level of catalyst receiver 8. The shaft of the handwheel 10 has adjustable spaced stops 11 which are specifically measured to bring inlet and outlet ports exactly into communication. Purging connection 12 allows for the introduction of inert gas for purging to insure that the atmosphere of the environment within the fixed bed reactors remains unchanged. Packing 13 is located at several levels throughout the length of catalyst sampler 1 between outer tube 2 and inner tube 4 to insure that catalyst does not enter the annulus between 2 and 4.

Figure 2:
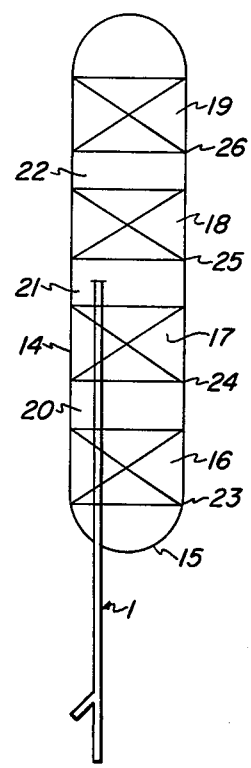
FIG. 2 is a schematic representation of the device as it fits into a fixed bed reactor.

In FIG. 2 is shown a cross-sectional view of the structure of the fixed bed reaction vessel and in particular shows a typical arrangement of multiple beds in an elongated vessel. Catalyst sampler 1 enters elongated vessel 14 through the curved bottom 15 of the elongated vessel and passes through one or more fixed bed regions of the vessel 16, 17, 18, 19, the top of catalyst sampler 1 terminating in one of the spaces 20, 21, 22 between the enumerated fixed bed regions. Catalyst is supported in the enumerated fixed bed regions 16, 17, 18, 19, by means of wire mesh screens 23, 24, 25, 26. It is a particular object of this invention to insure that the top of the catalyst sampler terminate in one of the enumerated empty spaces between the enumerated fixed bed catalyst regions. This will allow for the venting of the catalyst sampler with inert gases through the top of the sampler.

Figure 3:
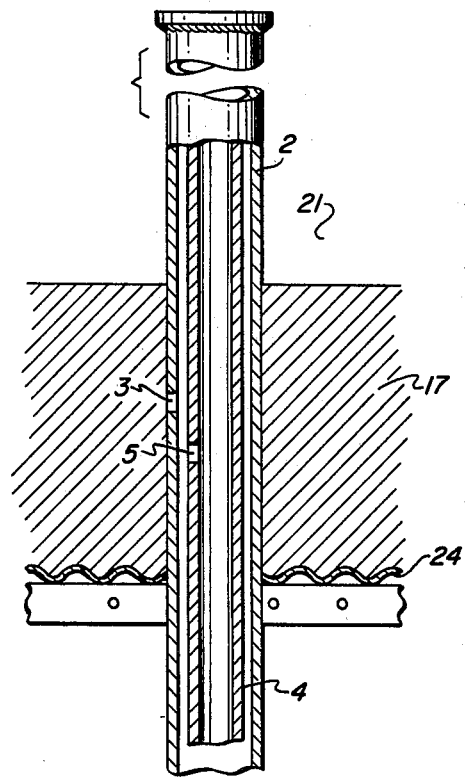
FIG. 3 is an enlargement of the inlet ports within a catalyst containing region of a fixed bed reactor.

FIG. 3 shows an enlarged view of one of the fixed bed regions, e.g. 17, the empty space region directly above fixed bed region, e.g. 21 and wire mesh screen, e.g. 24. As is shown outer tube inlet port 3 terminates within a fixed bed region 17. Referring to FIG. 1, there are shown stops 11 which are specifically measured to bring inlet and outlet ports exactly into communication. When it is desired to retrieve a sample of paticulate matter, handwheel 10 is rotated to one of the stops 11, thereby bringing inner tube inlet ports 5 into communication with outer tube inlet port 3. At this point the inner tube outlet means is out of engagement with the outer tube outlet means. When outer tube inlet ports 3 and inner tube inlet ports 5 are brought into communication, catalyst enters inner tube 4 and falls by gravity to the level of inner tube outlet port 7. The ports may be slanted upward to facilitate gravity flow. It is also possible to install a purge gas stream with outer tube inlet port 3 and inner tube inlet ports 5 in alignment to facilitate the flow of particulate matter into inner tube 4. A concentric guide means 30 is located between inner tube 4 and outer tube 2 to insure that the tubes remain concentric. After catalyst has entered inner tube 4, the handwheel is turned until it reaches another stop 11 which brings inner tube outlet port 7 into communication with outer tube outlet ports 6. At this point inner tube inlet means is out of engagement with the outer tube inlet means. This allows the catalyst to flow via gravity into catalyst receiver 8. Catalyst receiver 8 contains block valve 9 which allow the sealing off of both the lower portion of catalyst sampler 1 and catalyst receiver 8 to insure that no contamination enters either the catalyst receiver or the fixed bed reactor through the bottom of the catalyst sampler.

Inert gas can enter the system through purging connection 12 for purging of the annulus between outer and inner tubes 2 and 4. This purging can occur before and after the sample is retrieved to insure that atmospheric contaminants do not enter the system or the retrieved catalyst.

What is claimed is:

1. An apparatus for retrieving particulate matter from one level of a fixed bed reactor containing particulate beds spaced apart in an elongated vessel, such apparatus comprising:
   (a) an elongated inner tube slidably disposed within an outer tube which extends upwardly through said vessel and passes through said fixed beds of particulate matter, the top of said outer tube terminating in an empty space between said particulate beds to permit venting of said tubes through the top and also avoid thermal and bed weight distortion of said outer tube, said inner and outer tubes each having inlet and outlet means for transmitting particulate matter therethrough, said outer tube secured to said vessel and forming a pressure-tight connection therewith;
   (b) a shaft of a handwheel having adjustable spaced stops which are specifically measured whereby when said handwheel has been rotated to one of said stops said inner tube inlet means is in communication with said outer tube inlet means and said inner tube outlet means is out of engagement with said outer tube outlet means, and whereby when said handwheel is rotated to another of said stops said outer tube outlet means is in communication with said inner tube outlet means and said inner tube inlet means is out of engagement with said outer tube inlet means; and
   (c) means for collecting said particulate matter, said means being connected in pressure sealed engagement with said outer tube outlet means.

2. The apparatus of claim 1 wherein said inlet and outlet means are slanted upward to facilitate the flow of particulate matter by gravity to the bottom of said inner tube.

3. The apparatus of claim 2 wherein the inlets of said inner and outer tubes are both situated within said particulate bed.

4. The apparatus of claim 1 with the addition of means for applying a purge stream.

5. The apparatus of claim 4 wherein said particulate beds are beds of catalyst.

* * * * *